US006508984B1

(12) United States Patent
Turner et al.

(10) Patent No.: US 6,508,984 B1
(45) Date of Patent: Jan. 21, 2003

(54) SYSTEM FOR CREATING AND TESTING NOVEL CATALYSTS, REACTIONS AND POLYMERS

(75) Inventors: Howard W. Turner, Campbell, CA (US); Lynn VanErden, Livermore, CA (US); G. Cameron Dales, Palo Alto, CA (US); Adam Safir, Oakland, CA (US); Ralph B. Nielsen, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 72 days.

(21) Appl. No.: 09/620,310

(22) Filed: Jul. 19, 2000

Related U.S. Application Data

(62) Division of application No. 09/227,558, filed on Jan. 8, 1999
(60) Provisional application No. 60/080,652, filed on Apr. 3, 1998.

(51) Int. Cl.$^7$ ............................................. G01N 21/00
(52) U.S. Cl. ..................... 422/65; 422/130; 422/50; 422/68.1; 436/43; 436/37; 700/218; 700/213
(58) Field of Search ...................... 422/65, 130; 436/37; 700/218

(56) References Cited

U.S. PATENT DOCUMENTS

| 4,752,597 A | 6/1988 | Turner ........................ 502/104 |
| 5,064,802 A | 11/1991 | Stevens et al. ............. 502/155 |
| 5,198,401 A | 3/1993 | Turner et al. ............... 502/155 |
| 5,244,763 A | 9/1993 | Nielsen et al. ................ 430/72 |
| 5,278,119 A | 1/1994 | Turner et al. ............... 502/155 |
| 5,318,935 A | 6/1994 | Canich et al. .............. 502/117 |
| 5,447,895 A | 9/1995 | Marks et al. ................ 502/117 |
| 5,470,927 A | 11/1995 | Turner et al. ................ 526/126 |
| 5,470,993 A | 11/1995 | Devore et al. ................. 556/11 |

(List continued on next page.)

FOREIGN PATENT DOCUMENTS

| EP | 0 882 500 | 12/1998 | ............ B01J/19/00 |
| WO | WO 96/11878 | 4/1996 | |
| WO | WO 96/13529 | 5/1996 | |
| WO | WO 96/23010 | 8/1996 | |
| WO | WO 97/32208 | 9/1997 | |
| WO | WO 98/03521 | 1/1998 | |
| WO | WO 98/12156 | 3/1998 | |
| WO | WO 98/40159 | 9/1998 | ............ B01J/19/00 |

OTHER PUBLICATIONS

J. Ostresh et al. "Libraries from Libraries: Chemical Transformation of Combinatorial Libraries to Extend the Range and Repertoire of Chemical Diversity" Proc. Natl. Acad. Sci. USA, vol. 91, (Nov. 1994) pp. 11138–11142.

(List continued on next page.)

Primary Examiner—Jill Warden
Assistant Examiner—Brian Sines
(74) Attorney, Agent, or Firm—Senniger, Powers, Leavitt & Roedel

(57) ABSTRACT

A method and system for researching and developing and/or optimizing new catalysts and products in a combinatorial manner is disclosed. The method begins with starting components or a ligand library and provides methods of creating catalyst or product libraries, which are then tested in a reaction of interest. The system uses methods of robotic handling for moving libraries from station to station. The method and apparatus are especially useful for synthesizing, screening, and characterizing combinatorial catalyst libraries, but also offer significant advantages over conventional experimental methods as well.

8 Claims, 7 Drawing Sheets

U.S. PATENT DOCUMENTS

| | | | |
|---|---|---|---|
| 5,474,796 A | 12/1995 | Brennan | 427/2.13 |
| 5,495,036 A | 2/1996 | Wilson et al. | 556/12 |
| 5,502,017 A | 3/1996 | Marks et al. | 502/103 |
| 5,504,049 A | 4/1996 | Crowther et al. | 502/117 |
| 5,550,094 A | 8/1996 | Ali et al. | 502/115 |
| 5,594,047 A | 1/1997 | Nielsen et al. | 523/315 |
| 5,599,761 A | 2/1997 | Turner | 502/152 |
| 5,646,084 A | 7/1997 | Patton et al. | 502/152 |
| 5,679,548 A | 10/1997 | Barbas et al. | |
| 5,985,214 A | 11/1999 | Stylli et al. | 422/65 |
| 5,985,356 A | 11/1999 | Schultz et al. | |
| 6,030,917 A | 2/2000 | Weinberg et al. | 502/104 |
| 6,045,755 A * | 4/2000 | Lebl et al. | 422/65 |
| 6,253,118 B1 * | 6/2001 | Koyama | 700/218 |
| 6,267,930 B1 * | 7/2001 | Ruediger et al. | 422/130 |
| 6,333,196 B1 * | 12/2001 | Willson, III | 436/37 |

OTHER PUBLICATIONS

DeWitt, S. H., et al., "Combinatorial Organic Synthesis Using Parke–Davis's Diversomer Method," Acc. Chem. Res., vol. 29, No. 3, (1996) pp. 114–122.

Burger, Matthew T., et al., "Synthetic Ionophores, Encoded Combinatorial Libraries of Cyclen–Based Receptors for $Cu^{2+}$ and $Co^{2+}$, " J. Org. Chem., vol. 60, pp. 7382–7383, (1995).

Burgess, Kevin, et al., "New Catalysts and Conditions for a C–H Insertion Reaction Identified by High Throughput Catalyst Screening," Angew. Chem. Ind. Ed. Engl., vol. 35, No. 2, pp. 220–222, (1996).

Cole, Bridget M., et al., "Discovery of Chiral Catalysts through Ligand Diversity: Ti–Catalyzed Enantioselective Addition TMSCN to meso Epoxides," Angew. Chem. Int. Ed. Engl., vol. 35, No. 15, pp. 1668–1671, (1996).

Francis, Mathew B., et al., "Combinatorial Approach to the Discovery of Novel Coordination Complexes," J. Am. Chem. Soc., vol. 118, pp. 8983–8984, (1996).

Gennari, Cesare, et al., "Combinatorial Libraries: Studies in Molecular Recognition and the Quest for New Catalysts," Liebigs Ann./Recueil, pp. 637–647, (1997).

Gilbertson, Scott R., et al., "Synthesis of Phosphine–Rhodium Complexes Attached to a Standard Peptide Synthesis Resin," Organometallics, vol. 15, pp. 4678–4680, (1996).

Gilbertson, Scott R., et al., "The Combinatorial Synthesis of Chiral Phosphine Ligands," Tetrahedron Letters, vol. 37, No. 36, pp. 6475–6478, (1996).

Gilbertson, Scott R., et al., "Versatile Building Block for the Synthesis of Phosphine–Containing Peptides: The Sulfide of Diphenylphosphinoserine," J. Am. Chem. Soc., vol. 116, pp. 4481–4482, (1994).

Guerin et al., "Conformationally Rigid Diamide Complexes: Synthesis and Structure of Tantalum (III) Alkyne Derivatives," Organometallics, 1995, 14, 3154–3156.

Hsieh–Wilson, Linda C., et al., "Lessons from the Immune System: From Catalysts to Materials Science," Acc. Chem. Res., vol. 29, No. 3, pp. 164–170, (1996).

Johnson et al., "New Pd(II)– and Ni(II)–Based Catalysts for Polymerization of Ethylene and α–Olefins," J. Am. Chem. Soc., 1995, 117, 6414–6415.

Liu, Guangcheng, et al., "A General Solid–Phase Synthesis Strategy for the Preparation of 2–Pyrrolidinemethanol Ligands," J. Org. Chem., vol. 60, pp. 7712–7713, (1995).

Malin, Reinhard, et al., "Identification of Technetium–99m Binding Peptides Using Combinatorial Cellulose–Bound Peptide Libraries," J. Am. Chem. Soc., vol. 117, pp. 11821–11822, (1995).

Menger, F.M., et al., "Phosphatase Catalysis Developed via Combinatorial Organic Chemistry," J. Org. Chem., vol. 60, pp. 6666–6667, (1995).

Menger, Fredric M., et al., "A Combinatorially Developed Reducing Agent," Chem. Commun., pp. 633–634, (1996).

Moates, et al., Ind. Eng. Chem. Res., 35: 4801–4803 (1996), Infrared Thermographic Screening of Combinatorial Libraries of Heterogeneous Catalysts.

Molecular Diversity and Combinatorial Chemistry, Chaiken, Irwin M and Janda Kim D. (Eds.), American Chemical Society, Washington, DC, USA, Chapter 12, pp. 128–136, (1996).

Reetz, Manfred T., et al., "Time–Resolved IR–Thermographic Detection and Screening of Enantioselectivity in Catalytic Reactions," Angew. Chem. Ind. Ed., vol. 37, No. 19, pp. 2647–2650, (1998).

Roach, Peter L., et al., "Crystal structure of isopenicillin N synthase is the first from a new structural family of enzymes," Nature, vol. 375, pp. 700–704, 1995.

Schlögl, Robert, "Combinatorial Chemistry in Heterogeneous Catalysis: A New Scientific Approach to the King's New Clothes," Angew. Chem. Ind. Ed., vol. 37, No. 17, pp. 2333–2336, (1998).

Scollard et al., "Living Polymerization α–Olefins by Chelating Diamide Complexes of Titanium," J. Am. Chem. Soc., 1996, 118, 10008–10009.

Senkan, Selim M., "High–Throughput Screening of Solid–State Catalyst Libraries," Nature, vol. 394, pp. 350–353, (1998).

Shibata, Noro, et al., "Resin–bound peptide libraries showing specific metal ion binding," Bioorg. Med. Chem. Lett., vol. 7, pp. 413–416, 1997.

Shimizu, Ken D., et al., "Search for Chiral Catalysts Through Ligand Diversity: Substrate–Specific Catalysts and Ligand Screening on Solid Phase," Angew. Chem. Int. Ed. Engl., vol. 36, No. 16, pp. 1704–1707, (1997).

Sie, S.T., "Miniaturization of Hydroprocessing Catalyst Testing Systems: Theory and Practice," AIChE Journal, vol. 42, No. 12, pp. 3498–3507, (1996).

Taylor, Steven J., et al., "Thermographic Selection of Effective Catalysts from an Encoded Polymer–Bound Library," Science, vol. 280, pp. 267–270, (1998).

Thompson, Lorin A., et al., "Straightforward and general method for coupling alcohols to solid supports," Tetrahedron Letters, vol. 35, No. 50, pp. 9333–9336, 1994.

Xiang, X.–D., et al., "A Combinatorial Approach to Materials Discovery," Science, vol. 268, pp. 1738–1740, (1995).

* cited by examiner

SYSTEM FOR CREATING AND TESTING NOVEL CATALYSTS, REACTIONS AND POLYMERS

This application is a divisional application of U.S. patent application Ser. No. 09/227,558, filed Jan. 8, 1999, which is incorporated herein by reference and which claims the benefit of U.S. Provisional Application No. 60/080,652, filed Apr. 3, 1998, the teachings of which are incorporated herein by reference.

BACKGROUND

1. Technical Field

The present invention relates to the field of research for new catalysts or polymers or processes for making polymers. More particularly, this invention is directed toward an apparatus and method of performing homogeneous and supported homogeneous catalysis and related techniques for rapidly creating and testing catalyst libraries prepared by combinatorial techniques. This invention is also directed toward an apparatus and method for making polymers using combinatorial techniques.

2. Discussion

Combinatorial chemistry has revolutionized the process of drug discovery. See, for example, 29 *Acc. Chem. Res.* 1–170 (1996); 97 Chem. Rev. 349–509 (1997); S. Borman, *Chem. Eng. News* 43–62 (Feb. 24, 1997); A. M. Thayer, *Chem. Eng. News* 57–64 (Feb. 12, 1996); N. Terret, 1 *Drug Discovery Today* 402 (1996)). Because of its success in eliminating the synthesis bottleneck in drug discovery, many researchers have come to narrowly view combinatorial methods as tools for creating structural diversity. Few researchers have emphasized that, during synthesis, variations in temperature, pressure, ionic strength, and other process conditions can strongly influence the resulting properties of library members. For example, reaction conditions are particularly important in formulation chemistry and polymer chemistry, where one combines a set of components under different reaction conditions or concentrations to determine their influence on product properties.

Recently, combinatorial approaches have been used for discovery programs unrelated to drugs. Combinatorial materials science generally refers to the methods for creating a collection of chemically diverse compounds or materials and to methods for rapidly testing or screening this library of compounds or materials for desirable performance characteristics and properties. For example, some researchers have recognized that combinatorial strategies offer promise for the discovery of inorganic compounds such as high-temperature superconductors, magnetoresistive materials, luminescent materials, and catalytic materials. See, for example, co-pending U.S. patent application Ser. No. 08/327,513 "The Combinatorial Synthesis of Novel Materials" (published as WO 96/11878) and U.S. Pat. No. 5,776,359, which are both herein incorporated by reference. Compared to traditional discovery methods, combinatorial methods sharply reduce the costs associated with preparing and screening each candidate material.

Some combinatorial research into catalysis and polymer formation has begun. See U.S. patent application Ser. No. 08/898,715 "Combinatorial Synthesis and Analysis of Organometallic Compounds and Catalysts" (published as WO 98/03251). The following articles discuss one or more combinatorial techniques in conjunction with catalysis, and each are incorporated herein by reference: Senkan, *Nature*, vol 394, pp. 350–353 (Jul. 23, 1998); Burgess et al., *Angew. Chem. Int. Ed. Eng.*, 1996, 35, No. 2, pp. 220–222; Maier et al., *Angew. Chem. Int. Ed. Eng.*, 1998, 37, No. 19, pp. 2644–2647; Reetz et al., *Angew. Chem. Int. Ed. Eng.*, 1998, 37, No. 19, pp. 2647–2650; Schlögl, *Angew. Chem. Int. Ed. Eng.*, 1998, 37, No. 17, pp. 2333–2336; Morken et al., *Science*, vol. 280, pp. 267–270 (Apr. 10, 1998); and Gilbertson et al., *Tetrahedron Letters*, vol. 37, no. 36, pp. 6475–6478 (1996).

What is needed is a combinatorial method and apparatus for the research, discovery and development of catalysts and polymers. This invention advances the field by providing an entire system, beginning with a ligand library or a set of reactants and ending with screens for performance, with a variety of reaction and screening options.

SUMMARY OF THE INVENTION

This invention provides methods and apparatus for performing the combinatorial synthesis of libraries and screening of those combinatorial libraries. This invention gives those of skill in the art a variety of synthesis and screening techniques so that a complete combinatorial discovery or optimization research and development program can be successfully implemented for many different reactions, including all types of polymerizations or small molecule catalysis. The broadest concept of the methodology is that a library is created that is screened for a property or compound of interest. The libraries that are created depend on the reaction of interest, but are typically either catalyst libraries or product libraries. This invention provides a number of embodiments for performing such synthesis and screening and the embodiments may be combined together.

One embodiment of the present invention is a method and apparatus for researching for novel catalysts by starting with a ligand library that includes a plurality of member ligands. In the ligand library (also referred to as a parent ligand library) each ligand member may have a common scaffold, but will vary in structural diversity. The ligand library may also include ligand members that have different scaffolds. The important point is that the ligand library includes ligand members that are different from each other by either scaffold or structural diversity or both. Optionally, one or more daughter libraries are created from the parent ligand library by taking one or more aliquots from one or more member ligands in said ligand library. For example, each daughter library may be considered to be a replica of the ligand library, but each daughter ligand member would be smaller than the parent ligand member in terms of either volume or moles or mass. At least one metal precursor is added to at least a portion of the members of the ligand libraries or daughter libraries to create one or more catalyst libraries. The catalyst library is subjected to a reaction of interest. The reaction of interest may be a reaction that creates a product library. For example, if the reaction of interest is a polymerization reaction, a polymer library will be the result. Alternatively, the reaction of interest may be a screen for activity. The reaction of interest can have process conditions that are combinatorialized, such as varying amounts of reactants or different conditions (such as time, temperature, pressure, atmosphere, etc.). The method optionally provides different screening stages, such as a primary screen to eliminate some members from a library from going on to a secondary screen.

In another embodiment, mixtures of starting components (such as ligands, metal precursors, initiators, monomers, solvents, etc.) are combined in different ratios. A reaction of interest is performed under varying conditions to create a product array. This embodiment focuses on combinatorializing the conditions of the reaction of interest. Process conditions that may be combinatorialized include amounts (volume, moles or mass) and ratios of starting components, time for reaction, reaction temperature, reaction pressure, rate of starting component addition to the reaction, residence time (or product removal rate), reaction atmosphere, reaction stir rate and other conditions that those of skill in the art will recognize. The library that is created in this embodiment is a product library that is then screened for a property or compound of interest. Optionally, prior to screening, the product library is daughtered into one or more daughter product libraries.

In addition, the two above embodiments can be combined together. For example, this invention may be practiced in order to discover a polymer of interest by free radical polymerization (e.g., a polymer having predetermined properties, such as molecular weight or particle size). The library of polymers (e.g., a product library) may be created by having diversity in the starting components used or by having diversity the reactions conditions (e.g., time, temperature, mixing speed, etc.). The polymer library is then tested to determine if a polymer of interest has been created using one of many different rapid polymer characterization techniques. Thus, in this example, the screen may be the reaction, the polymer characterization or both.

The embodiments of this methodology are combined into a flexible system that includes a number of different stations including one or more stations for combining starting materials, daughtering the libraries, performing the reactions of interest and screening the results of the process. The system includes a control system that controls, monitors and directs the activities of the system so that a user may design an entire series of experiments by inputting library design, screening or data manipulation criteria.

Those of skill in the art will appreciate the variety of methods for creating diversity in the libraries of this invention. The screens that are provided to determine if the diversity has produced a product of interest complete the research and development methodology.

A further understanding of the nature and advantages of the present invention may be realized by reference to the remaining portions of the specification and the drawings.

DETAILED DESCRIPTION

Figure 1A:
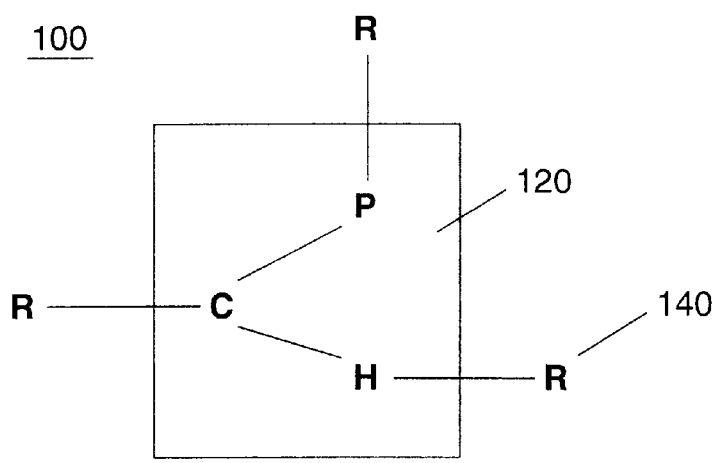
FIGS. 1A and 1B show a generic ligand having a scaffold and structural diversity and a ligand library, respectively.

There are two principal features to this invention: (1) creating a library having diversity and (2) screening that library for a property or compound of interest. A library in this invention has either chemical diversity or process diversity. Chemical diversity refers to a library having members that vary in atoms or molecules. Process diversity refers to a library having members that may have begun with the same atoms or molecules, but with members that have been subjected to different processing conditions and are different as a result of those different processing conditions. Different processing conditions include varying amounts (volume, moles or mass) and ratios of starting components, time for reaction, reaction temperature, reaction pressure, rate of starting component addition to the reaction, residence time (or product removal rate), reaction atmosphere, mixing or stir rate and other conditions that those of skill in the art will recognize. It is through the creation of libraries having diversity and the screening of that diversity for a property or compound of interest that a complete combinatorial research and development program may be undertaken for homogeneous catalysis or supported homogeneous catalysis or initiated polymerization reactions.

In one embodiment, this invention is directed to rapid creation and testing of novel catalysts, but offers significant advantages over conventional experimental methods and systems. For example, the present invention allows for automated parallel catalyst creation and screening of multiple synthetic routes to targeted catalysts, thereby saving time and conserving valuable reactants in determining appropriate catalysts for catalyzing a pre-selected reaction. This invention also provides a variety of screening options, allowing for flexibility in choosing the appropriate reaction flow and conditions for a reaction of interest.

For example, if a coordination polymerization reaction is the reaction of interest, this invention provides the method and apparatus for the synthesis of organometallic complex libraries by a variety of routes that may be catalysts. Optional activation of those organometallic complexes into catalysts is included. After the catalyst libraries are prepared the invention provides for screening of the catalyst libraries. Screening may be in, for example, a parallel polymerization reactor that provides detailed information about catalytic activity under a variety of reaction options and conditions, including monomer and comonomer choice, solvent, pressure, temperature, stirring rate, volume, stoichiometric relationships and order of addition of chemicals. Thus, one may chose to "combinatorialize" the polymerization reaction conditions for a single catalyst library. Optional steps in this example coordination polymerization combinatorial process include a primary screen prior to screening in the parallel polymerization reactor. A primary screen may, for example, comprise an optical screen under polymerization conditions that simply determines which members of the catalyst library have any activity. Another optional step is to further characterize the resultant polymers formed in the parallel polymerization reactor. Such further screening may employ a rapid liquid chromatography and/or light scattering system, such as those described in U.S. Provisional Application No. 60/080,652, filed Apr. 3, 1998, which is incorporated herein by reference. Such a further screen may also determine the physical or melt flow properties of the resultant polymers, such as with a sensor-array based system such as is disclosed in U.S. patent application Ser. No. 09/210,485, filed Dec. 11, 1998, which is incorporated herein by reference.

Thus, the flexibility of this invention can be seen by those of skill in the art from the variety of options that a complete system offers, including choosing starting components (e.g., ligands and metal precursors), choosing reaction or coordination routes for the creation of catalyst libraries, choosing screening reactors and reaction conditions and choosing characterization methods and apparatus.

In other embodiments, this invention discloses methods for rapidly forming polymer product libraries from at least an initiator and a monomer. A variety of monomers and initiators can be chosen, along with other polymerization additives, such as solvents, co-initiators, modifiers, surfactants, etc. Those of skill in the art know of such additives. A parallel reactor is used for the reaction and the parallel reactor may have internal sensing capabilities providing real time property characterization for certain properties, such as viscosity. The parallel reactor may also provide the ability to vary reaction conditions from one reactor vessel to another so that the polymerization conditions may be combinatorialized. The polymer libraries may then be further characterized using rapid polymer characterization techniques. Thus again, the flexibility of this invention can be seen by those of skill in the art from the variety of options that a complete system offers, including choosing initiators, choosing monomers, choosing methods and conditions of reaction for the creation of polymer libraries, and choosing characterization methods and apparatus. In this manner a complete combinatorial polymer discovery or optimization research and development program may be undertaken.

As discussed herein there are three fundamental types of libraries: a ligand library, a catalyst library and a product library. The three types of libraries may or may not be used in the same embodiment of the invention.

A ligand library is a library comprised of member ligands. Typically, a ligand library has chemical diversity. As used herein, chemical diversity within the ligand library is divided up between a variety of scaffolds and structural diversity elements. Referring to FIG. 1A, member ligands 100 of the ligand library 10 include a scaffold 120, which those of skill in the art may also refer to as a backbone. There is at least one scaffold in a parent ligand library. However, there may be 2, 3, 4, 5 or more different scaffolds in a ligand library. The number of scaffolds will depend on how the library was formed or how the library was stored. If, for example, ligands from different ligand synthesis procedures were stored together as a single library, the ligand library will be the result of this combination and any number of desired ligand scaffolds may be included in the ligand library.

Also, there is a plurality of different ligands in a ligand library. Thus, if there is one scaffold there are typically at least four or five different structural diversity elements off of the scaffold. Referring to FIG. 1A, the structural diversity elements 140 are shown as R groups. The member ligands in the ligand library are typically stored or provided in a spatially addressable format, meaning that each ligand is separated from the others. However, pooled ligand libraries may also be used if catalytic activity can be separated to determine which catalyst caused certain observed activity, such as with a tagging or coding technique. See, e.g., U.S. application Ser. No. 09/033,207, filed Mar. 2, 1998, which is incorporated herein by reference.

Figure 1B:
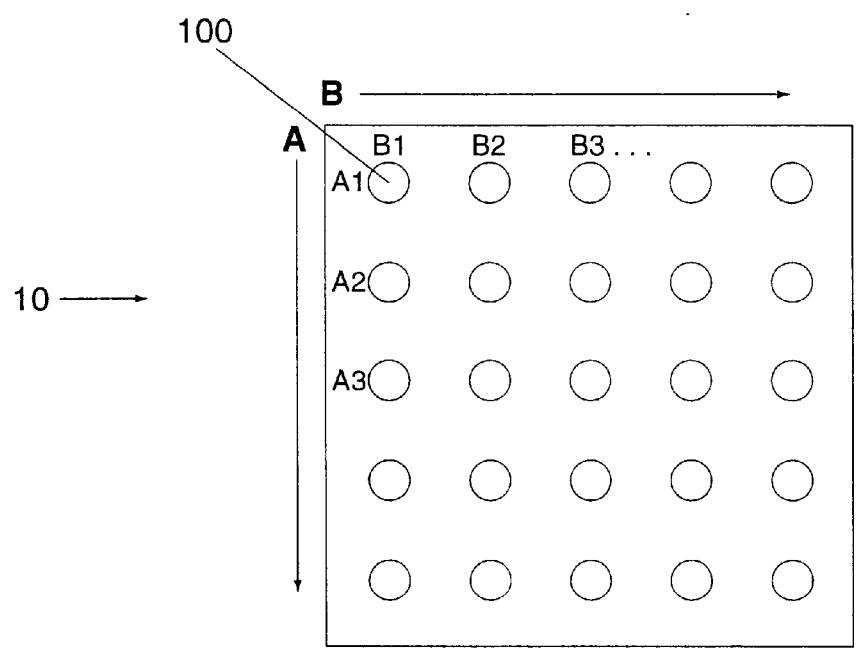

Thus, the ligand library 10, shown in FIG. 1B, may include ligand members having one scaffold in different columns, B1, B2, etc. along the B direction and may have differing structural diversity in different rows A1, A2, etc. along the A direction. In one embodiment of the present invention, the ligand library 10 is made up of a plurality of member ligands 100 that have a common scaffold with each member ligand being structurally diverse, as represented by the different positioning of R-groups 140 on scaffold 120 in FIG. 1A. In that embodiment, using the representation in FIG. 1B, only one column, e.g., B1, would be present in the patent library. In another embodiment, the ligand library is made up of member ligands having different scaffolds, wherein the ligand members in a scaffold group are structurally diverse, meaning B1, B2, B3, etc. are present in the ligand library. Of course, the ligand library may also include standards, blanks, controls or other members that are present for other reasons. Also, the ligand library may have two or more members that are identical as a redundancy option or when reaction conditions are to be combinatorialized. The member ligands of the ligand library are preferably solids so that the ligand library may be easily stored, however, the ligand libraries may also be stored in solution. When a solid phase stored ligand library is going to be used to create catalyst libraries, the solid member ligands may be dissolved in a suitable solvent.

There are many possible example ligand libraries. Several ligand libraries have been described in detail in copending, commonly assigned U.S. patent applications, including U.S. application Ser. No. 09/037,162, filed Mar. 9, 1998; U.S. application Ser. No. 09/119,318, filed Jul. 20, 1998; U.S. application Ser. No. 09/062,128, filed Apr. 17, 1998; U.S. application Ser. No. 09/168,772, filed Oct. 8, 1998; and U.S. application Ser. No. 09/146,206, filed Sep. 2, 1998. Each of these applications is incorporated herein by reference for all purposes.

The ligand library may be created by combinatorial chemistry methods similar to those that are described in co-pending U.S. patent application Ser. No. 08/327,513 "The Combinatorial Synthesis of Novel Materials" (published as WO 96/11878) and co-pending U.S. patent application Ser. No. 08/898,715 "Combinatorial Synthesis and Analysis of Organometallic Compounds and Catalysts" (published as WO 98/03251), which are both herein incorporated by reference. Others have disclosed methods for preparing enormous libraries of ligands. See for example U.S. Pat. Nos. 5,143,854, 5,424,186 and 5,288,514 and WO 92/10092, each of which are incorporated herein by reference. The method of synthesis of a parent ligand library is not critical to this invention. Indeed in some embodiments, ligand libraries may be purchased. One or more ligand libraries may be stored and retrieved from a storage rack for transfer to either the daughtering station or a diluting station or a dissolution station, as discussed below. Such retrieval and transfer to another station may be automated using known automation techniques, such as those disclosed in WO 98/40159, incorporated herein by reference. Robotic apparatus is commercially available, for example from Cavro, Tecan, Robbins, Labman, Bohdan or Packard, which are companies that those of skill in the art will recognize.

Figure 2:
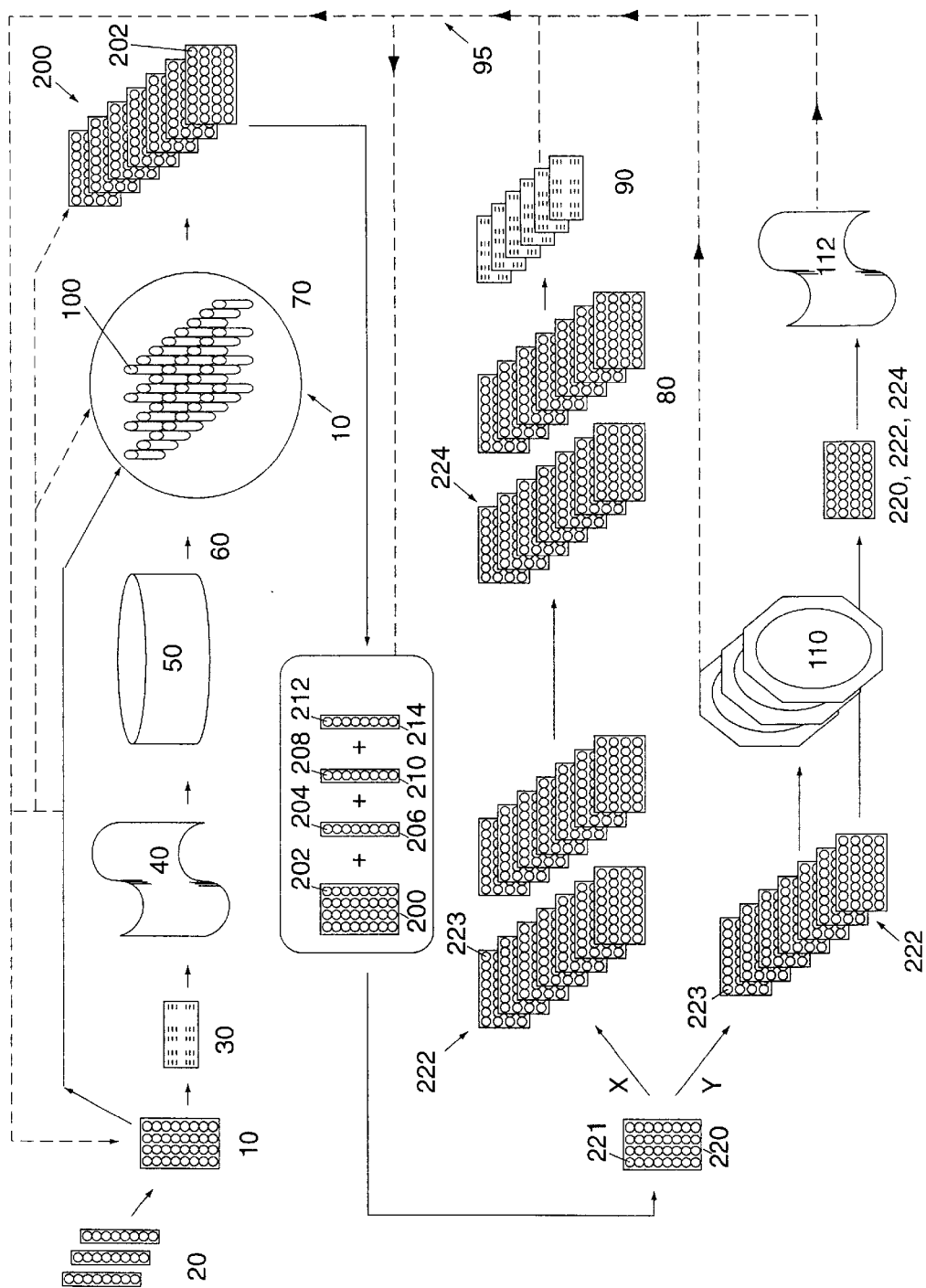
FIG. 2 is a flowchart depicting an overall method for one embodiment of the invention.

One option for the creation of the ligand library is shown in FIG. 2. Ligand precursors 20 are formed into a parent ligand library 10. The parent ligand library 10 is initially tested at a preliminary testing station 30 to determine if the desired ligand members have been synthesized successfully. There may be bulk manufacturing 40 and bulk storage 50 of the parent ligand library, so that each member is made in greater quantities and optionally stored for future multiple testing of the same parent library ligand members in different reactions of interest or under different reactions conditions or for combining with different metal precursors or activators or modifiers. In embodiments using bulk manufacture and storage, the ligand members in the ligand library may be in solid form. The solid ligand members are typically dissolved or diluted in a suitable solvent in a dissolution or dilution step 60 to provide the parent ligand library 10 with member ligands 100 in a liquid form at point 70 in FIG. 2. Dilution or dissolution may be manual or automatic, such as with known liquid handling robots. Other processing conditions of dissolution or dilution may also be controlled, such as using a glove box for an inert atmosphere during dilution or dissolution. The temperature of the operation may also be controlled by providing a heating/cooling block, such as that disclosed in commonly assigned U.S. application Ser. No. 09/417,125 filed Nov. 19, 1998 and incorporated herein by reference. In other embodiments, the ligand library is provided in a liquid form, for example with each ligand stored in a separate vial. In those embodiments, the parent ligand members may be stored in a vial having a septum that can be penetrated by a needle that may be on a robotic arm of known liquid handling robots. Optionally, as shown in FIG. 2 also, the bulk steps or storage can be eliminated so that the parent ligand library 10 goes directly from synthesis to point 70 in FIG. 2.

The next type of library is a catalyst library, which is a collection of potentially catalytic compounds or compositions. The members are potentially catalytic depending on the reaction of interest, i.e., a member may be active in one reaction of interest, but inactive in a different reaction of interest. The catalyst library is formed from the combination of ligands and metals. The catalyst library may be formed from the combination of a ligand library and a metal precursor. In other embodiments, the catalyst library is formed from the combination of a metal precursor library and a ligand. For example, combining comprises adding at least one ligand member from the ligand library to at least one metal precursor. More typically, at least four ligand members, at least 10 ligand members, at least 25 ligand members, at least 50 ligand members or at least 96 ligand members are provided that are each combined with at least one metal precursor. Also for example, combining comprises adding at least one metal precursor member from a metal precursor library to at least one ligand.

There are a number of methods for combining metal precursors with the ligand members of the library. In some embodiments, the same metal precursor is added to the ligand members (whether the members have different scaffolds or not) or different metal precursors are added to different ligand library members. In other embodiments, a different metal precursor is combined with each member ligand having a different scaffold such that the number of different metal precursors is equal to the number of different scaffolds. In still other embodiment, different metal precursors are added to ligand members having different structural diversity elements. Combining different metal precursors with different ligand library members provides the opportunity to try different routes for the formation of the same or similar metal-ligand complexes or compositions. In other embodiments, the ligand members will be mixed with a suitable metal precursor prior to or simultaneous with allowing the mixture to be contacted with the reactants in the next library or testing phase of the invention. When the ligand member is mixed with the metal precursor, a metal-ligand complex may be formed, which may be a catalyst.

Metal precursors may take the form of a metal atom, ion, compound or other metal precursor compound. In some embodiments, the member ligands may be combined with a metal precursor and the product of such combination is not determined, if a product forms at all. For example, the ligand member may be added to a reaction vessel at the same time as the metal or metal precursor compound along with additional reactants in the reaction of interest. As such, the result of the combination is not determined. The metal precursors may be characterized by the general formula $M(L)_n$ where M is a metal selected from the group consisting of Groups 3, 4, 5, 6, 7, 8, 9, 10, 11, 12, 13 and 14 of the Periodic Table of Elements. Specific metals include Sc, Y, La, Ti, Zr, Hf, C, Nb, Ta, Cr, Mo, W, Mn, Re, Fe, Ru, Os, Co, Rh, Ir, Ni, Pd, Pt, Cu, Ag, Au, Zn, Cd, Al, In, Tl and Sn. L is a metal-ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is charged, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, acetoxy, silyl, boryl, phosphino, amino, thio, seleno, and combinations thereof. When L is neutral, L is selected from the group consisting of carbon monoxide, isocyanide, dibenzylideneacetone, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. The ligand to metal precursor ratio is determined by the research program of interest, and for example may be in the range of about 0.01:1 to about 100:1, or more specifically in the range of about 0.5:1 to about 20:1.

Depending on the ligand library, it may be necessary to additionally combine a ligand modifier 208 with member ligands 202 of the ligand libraries, as shown in FIG. 2. If there are different ligand modifiers 208, they may be in a ligand modifier library 210 and may be added to the ligand libraries 200 at the same time as the metal precursor(s) or prior to serve to produce modified ligand libraries before combining the ligand members with the metal precursors to achieve the desired target catalysts. The purpose of a ligand modifier is to allow or assist the ligand to coordinate to or bond with a metal atom, ion or precursor. The ligand modifier is generally a deprotonation agent that modifies the ligand at the position(s) where the ligand coordinates to or bonds with the metal atom, ion or precursor. Ligand modifiers include deprotonating agents such as alkyl lithium compounds (such as methyl lithium or butyl lithium) and lithium diisopropyl amine. Those of skill in the art know many ligand modifiers that are useful in this invention.

Another option in forming the catalyst libraries is to provide an activator. When there is more than one activator, the activators may be provided in an activator library 214. The activator or activating technique includes the use alumoxanes, strong Lewis acids, compatible noninterfering activators and combinations of the foregoing. The foregoing activators have been taught for use with metal complexes in the following references, which are hereby incorporated by reference in their entirety: U.S. Pat. Nos. 5,599,761, 5,616, 664, 5,453,410, 5,153,157, 5,064,802 and EP-A-277,004.

There are a number of methods for combining the ligand modifiers or activators with the ligand libraries and metal precursors. In some embodiments, the same ligand modifiers or activators are added to the members of the daughter library (whether the members have different scaffolds or not) with the metal precursor. Alternatively, different ligand modifiers or activators are added to different ligand libraries.

In other embodiments, a different ligand modifier or activator is combined with each member ligand in the ligand libraries having a different scaffold such that the number of different ligand modifiers or activators is equal to the number of different scaffolds for each member ligand. In still other embodiment, different ligand modifiers or activators are added to daughter library members having different structural diversity elements. Combining different ligand modifiers or activators with different ligand members provides the opportunity to try different routes to the formation of the same or similar catalyst libraries.

Thus, combining ligands, metal precursors, optionally ligand modifiers and optionally activators (or activating techniques) provides those of skill in the art powerful options for following different chemical routes for the formation of the same or a similar catalyst. The use of different chemical routes to the same or similar catalyst in combinatorial materials science may minimize the chances of missing an active catalyst for a reaction of interest. One specific example of the use of different chemical routes for formation of the same or similar polymerization catalysts is in the field of cationic metallocene catalysts stabilized by compatible anions (see e.g., U.S. Pat. Nos. 5,599,761 or 5,817,849, both of which are incorporated herein by reference). One route to the formation of such catalysts is through the use of ion exchange activators. A second route is through the use of Lewis Acids. A third route is through the use of oxidative activators. The result of each route is an active catalyst having substantially the same structure, which produces substantially the same result under similar polymerization conditions.

A third type of library is a product library. A product library is the result of running a reaction of interest. Starting components are added to a reactor and a reaction of interest is run to form the product members of the product library. A product library obtains its diversity either by chemical diversity in the starting components or by process diversity or both and both types of diversity are discussed above. Thus, a product library may be the result of testing a catalyst library in a reaction of interest run under the same or different process conditions. A product library also may be the result of beginning with the same starting components and testing those components under different processing conditions. Specifically not within the scope of this invention is the formation of product libraries having members that are biological polymers, such as polymers made from alpha amino acids and nucleotides. Examples of polymers that may be members of a product library include homopolymers, copolymers or higher order polymers like polyethylenes, polyurethanes, polyesters, polycarbonates, polyacetates, polystyrenes, polyamides, and the like.

Starting components for forming a product library are those components needed for performing the reaction of interest. Reactions of interest include those selected from the group consisting of carbonylation, hydroformylation, hydroxycarbonylation, hydrocarbonylation, hydroesterification, hydrogenation, transfer hydrogenation, hydrosilylation, hydroboration, hydroarmination, epoxidation, aziridination, reductive amination, aryl amination, polymerization, oligomerization, C-H activation, insertion, C-H activation-insertion, C-H activation-substitution, C-halogen activation, C-halogen activation-insertion, C-halogen activation-substitution, cyclopropanation, alkene metathesis, and alkyne metathesis. Those of skill in the art know what starting components are needed for each of these types of reactions.

Starting components include catalysts, ligands, metal precursors, ligand modifiers and activators as discussed above. Starting components also include monomers, solvents, initiators, scavengers and surfactants/emulsifiers. Starting components that are monomers that have at least one addition-polymerizable unsaturated bond, including olefins, diolefins, allyl esters, vinyl ethers, vinyl esters, vinyl heterocyclic compounds, stryrenes, halogenated olefins, crotonic acids, vinyl ketones, itaconic acids and esters, unsaturated nitriles, acrylic or methacrylic acids and esters, acrylamides and methacrylamides and combinations thereof (see, e.g., U.S. Pat. No. 5,244,763, incorporated herein by reference). Example of solvents include polar and non-polar solvents and ionic solvents and may include alkanes, heterocyclic compounds, chlorinated compounds, water, and combinations thereof. Surfactants may be cationic, anionic, zwitterionic or non-ionic, including combinations thereof. Initiators may initiate a cationic, anionic or free radical reaction, and include inorganic salts, peroxy comounds and the like (see, e.g., U.S. Pat. No. 5,594,047, which is incorporated herein by reference). For example, for coordination polymerization, the starting materials include monomers, solvent, catalyst libraries (either activated or not) and scavengers. Also for example, for a free radical polymerization, the starting components comprise at least an initiator and a monomer. Other starting components include co-initiator, co-monomers, solvents, surfactants, emulsifiers or other additives. In forming a product library, the starting materials may be varied with respect to each other in terms of volume, moles or mass. In varying the starting materials, the types of ratios that can be varied include monomer to initiator; monomer A to monomer B; solvent to monomer; surfactant to initiator; catalyst to activator; and combinations thereof.

The product library has different members possibly as the result of combinatorializing the process variables in the reaction of interest. Process variables that may be combinatorialized include the amounts (volume, moles or mass) and ratios of starting components, time for reaction, reaction temperature, reaction pressure, rate and/or method of starting component addition to the reaction (or reactor), residence time (i.e., rate and/or method of product removal from the reaction or reactor), reaction stir rate and/or method, reaction kill rate and/or method, reaction atmosphere and other conditions that those of skill in the art will recognize. The product libraries are created using one of the parallel reactors discussed below, including the parallel solution reactor, the continuous feed reactor, the multi-temperature reactor block, the parallel batch reactor or another parallel reactor that may be known such as in U.S. Pat. No. 4,099,923, which is incorporated herein by reference.

Therefore, those of skill in the art will appreciate the vast number of different possible combinations of ligands, metal precursors, modifiers, activators or other starting components that may be combined together to form the catalyst libraries. In addition, this combination methodology may be combined with combinatorializing of various reaction conditions, including different starting component ratios, different temperatures, solvents, pressures, mixing rates, times, order of addition of chemicals or atmospheres to form vastly different product libraries. For example a multiple temperature reactor block, such as discussed below, may be used to provide different temperature and pressure options. Also optionally, the combining of ligands 202, metal precursors 204, modifiers 208 or activators 212 may take place in the reactor being used for the reaction of interest. Combining may be done just before the reaction of interest or may be done well before the reaction of interest.

In the methodology of this invention, a library is screened for a property or compound of interest. Depending on the embodiment being practiced, the screen may look for the existence of a particular compound or for a particular property. For example, when free radical polymerization is the reaction of interest, the screen may look for molecular weight or particle size. Also for example, when aryl amination is the reaction of interest, the screen may look for the amine that the reaction is intended to form. The screening may take place as the reaction of interest is being performed. As used herein, "screening" refers to testing a library for one or more properties or compounds or materials. Also as used herein, "reaction" refers to a chemical transformation (e.g., amination or polymerization). A screen may be combined with a reaction of interest, but the two may also be separate. For example, polymerization reactions performed in stirred tank parallel polymerization reactors are both a reaction and a screen because a polymerization reaction is performed and catalyst activity can be monitored by gas monomer uptake or by temperature increase or by an in-reactor sensor or by lag in a stirrer, providing testing of the properties of the catalyst or polymer. Also for example, a polymerization reaction performed in a batch reactor block would be considered to be only a reaction of interest if there is no monitoring as the reaction is proceeding. Also for example, nuclear magnetic resonance (NMR) or gas chromatography (GC) and mass spectrometry (MS) are only screens because they determine the results of the reaction of interest, which was performed in a separate reactor.

Each of the three types of libraries may be stored in a liquid or solid state and retrieved from storage for combining, daughtering, running in the reaction of interest or screening or combinations thereof. Libraries are preferably stored in a storage rack that holds the libraries separately from each other. Libraries may be retrieved from storage either manually or automatically, using known automated robots. Specific robots useful for retrieving such stored libraries include systems such as those marketed by Aurora Biosciences or other known robotic vendors. If the libraries are stored in the solid phase, the members typically require dissolution, which is performed at a dissolution station, which may be the combining station (discussed below) or may be in addition to the combining station. A dilution station is a location where the library members are dissolved in a suitable solvent for use in either the reaction of interest or in a screen.

Also, each of these types of libraries may be daughtered into one or more daughter ligand libraries, daughter catalyst libraries or daughter product libraries, respectively. A daughter library is created from the parent library at a daughtering station by taking one or more aliquots from one or more members in the parent library, wherein an aliquot is a definite fraction of a whole. This process is referred to as "daughtering." Literally, a liquid pipette, operated either manually or automatically (e.g., robotically), draws a bit of a member from the parent library and dispenses that aliquot into another container to give a daughter library member. A limited number of members of the parent library may be daughtered or all the members may be daughtered at least once to create one daughter library. Thus, a daughter library may be smaller than the parent library in terms of either mass, volume or moles and/or in terms of the number of members. In other embodiments, the members of the parent library are maintained in a solid form. During the daughtering process known solid handling equipment and methods are used to take the aliquot from the parent library to created the daughter library, which will have members that are also solids. Thereafter, it may be necessary to dissolve the members of the daughter libraries in a solvent. Daughtering is performed in order to provide multiple libraries for multiple reactions of interest or multiple screens without having to recreate the parent library.

Optionally a filtering station is provided, which is preferably a parallel filtering station. The filtering station is useful to filter off solid phase agents or products from liquid products or precursors. For example, in some embodiments the metal precursors will be provided in solid-phase form, such as the solid phase metal delivery agents disclosed in commonly assigned U.S. patent application Ser. No. 09/025, 841, filed Feb. 19, 1998, incorporated herein by reference. The solid-phase metal precursors allow for synthesis of the catalyst libraries in the solution phase and then filtering off the solid-phase metal precursor. A filtering station provides for ease in the synthesis of the catalyst libraries or the ligand libraries. The ligands, metal precursors, ligand modifiers or activators may be provided in the solid phase (e.g., on a bead or other support) allowing for ease in ligand or catalyst preparation. Solid phase combinatorial synthesis of ligands is well known. See, e.g., Ellman et al., "Solid-Phase Synthesis: Applications to Combinatorial Libraries", Annu. Rep. Med. Chem., 1996, 31, pp. 309–318; Rees et al. "Solid-Phase Organic Reactions: A review of the Recent Literature", Tetrahedron, Vo. 52, No. 13, pp. 4527–4554, 1996; and Kaldor and Siegel, "Combinatorial chemistry using polymer-supported reagents", Currents Opinion in Chemical Biology, 1997, 1:101–106; each of which are incorporated herein by reference. Solid phase agents or reagents in association with combining generally allows for the use of excess agents or reagents, ease of purification or work-up and automating the process.

Reactions of interest may be performed in a parallel reactor chamber or a parallel reactor block. Looking first at reactors that also contain screening capabilities, parallel reactors that are useful with this invention include a parallel solution reactor with internal sensing as disclosed in U.S. patent application Ser. No. 09/177,170, filed Oct. 22, 1998 and its improved version, U.S. patent application Ser. No. 09/211,982, filed Dec. 14, 1998. This reactor includes internal sensing and thus is also a screen. This parallel reactor allows for the variation of several different processing conditions, and therefore allows one to combinatorialize reaction conditions or process variables. For example, a mechanical resonator (e.g., a tuning fork) may be the sensor that detects product, compound, reactant or reaction properties. In another embodiment the parallel reactor may be a closed chamber with a tuning fork in the reactor, as disclosed in U.S. patent application Ser. No. 08/946,921, filed Oct. 8, 1997, which is incorporated herein by reference (published as WO 98/15501, which is also incorporated herein by reference).

Another parallel reactor that also includes screening capability is an optical screen, using infrared (IR) thermography or Fourier Transform Infrared (FTIR) spectroscopy or visible light or other optical viewing as disclosed in copending U.S. patent application Ser. No. 08/946,135, filed Oct. 7, 1997, (published as WO 98/15815) or in copending U.S. patent application Ser. No. 08/947,085, and filed Oct. 8, 1997, (published as WO 98/15805). These applications are incorporated herein by reference. Using an optical technique typically entails inserting the starting materials (e.g., catalyst library member with reactants or initiator with monomer) in an array format into a chamber (for example, a vacuum chamber or a chamber pressurized with reactant monomer or a chamber pressurized with an inert gas). The reaction of interest is performed in parallel in the chamber using a plate having multiple wells for the catalyst members or starting materials for the product members (such as a microtiter plate, for example). The chamber has a window that is invisible to the optical camera (e.g., calcium fluoride or saphire crystal for an IR camera). As the reaction of interest is carried out, the optical camera monitors the reaction with active catalyst or polymer members meeting a specified property or characteristic. Alternatively, for example, a dye may be inserted into the reactor vessel array and the camera may monitor a color change. Also for example, an IR camera may monitor heat of reaction for exothermic reactions.

Another reactor/screen is related to thin layer chromatography ("TLC"), as described more fully in U.S. patent application Ser. No. 09/149,586, filed Sep. 8, 1998, entitled "Sampling and Analysis of Reactions by Trapping Reaction Components on a Sorbent," incorporated herein by reference. In TLC screening, a reactant is added to the members of the catalyst library, thereby causing a reaction. A thin layer of sorbent is disposed on the plate, so as to cover the wells containing the catalysts. Vapor product resulting from the reactions then contacts the sorbent in discrete areas (heating may be necessary). In some cases, visual inspection is sufficient to determine active catalysts. But, a use of a commercially available florescent indicator reagent may be sprayed onto the sorbent, with the sorbent being exposed to ultra-violent light. A charge-coupled device camera or spectrum analyzer then captures intensity readings of the products on the sorbent to indicate which particular catalysts are desirable for those reactions.

Figure 3:
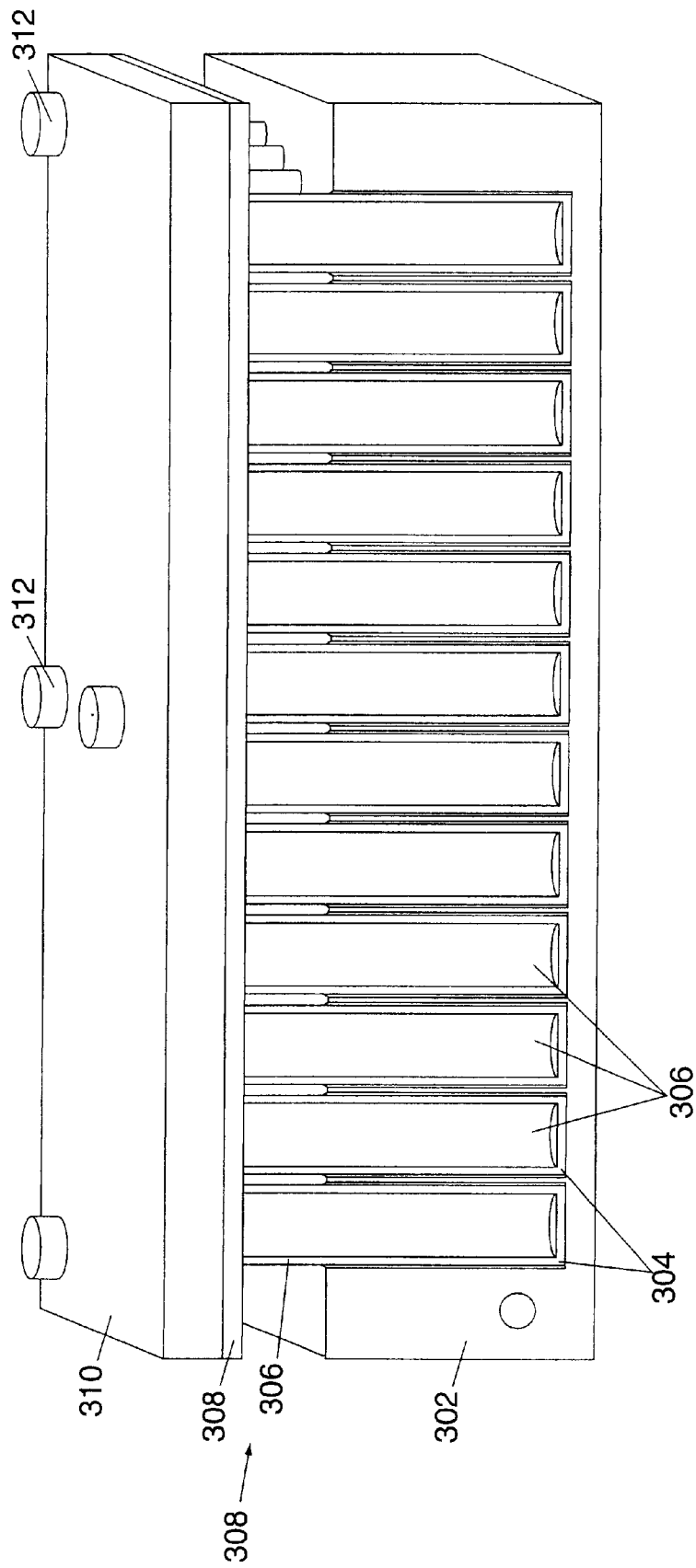
FIG. 3 is a cut-away perspective illustration of a glass lined parallel batch reactor useful in this invention.

Turning to reactors that do not include screening, other parallel reactors useful in this invention include a multi-temperature parallel reactor as disclosed in U.S. patent application Ser. No. 09/417,125, filed Nov. 19, 1998 and a continuous feed parallel reactor as disclosed in U.S. patent application Ser. No. 09/205,071, filed Dec. 4, 1998. These applications are incorporated herein by reference. These reactors typically include the ability to combinatorialize certain process variables, such as temperature, time, feed rate, mixing rate, etc. Of course, the reactants, catalysts, initiators, etc. can also be modified or combined in different amounts (different moles, volume or mass). Another parallel reactor useful in this invention is a parallel batch reactor. Such a reactor is shown in FIG. 3. FIG. 3 shows a batch reactor 300 having a reactor block 302 with a plurality of wells 304 for receiving a plurality of reactor vessels 306. To seal the reactor vessels 304, a sheet 308 is placed over the top lip of the plurality of reactor vessels 306 and a top plate 310 is fastened to the reactor block 302. Fastening may be by bolts, clips, clamps, wing nuts or other fastening methods known to those of skill in the art. Bolts 312 are shown in FIG. 3 as the fastening method and the bolts 312 are screwed into threads drilled into the reactor block 302. Materials useful as the reactor block and top plate include aluminum, steel or other metals, with aluminum being preferred for its thermal transfer properties. The reactor vessels 306 may be plastic or glass, with glass being preferred. The sheet 308 is typically made from a material that is chemically resistant to the reaction of interest taking place in the reactor vessels as well as being elastic for its sealing properties. The sheet 308 may be selected from the group consisting of Teflon®, silicone rubber, Vitron®, Kalrez® or equivalents. Parallel batch reactors of this type are useful for the reactions of interest discussed above, and may be heated. Mixing/stirring balls may be added to the parallel batch reactor, which may then be placed on a rocking or rotating plate fixed with a heating element for mixing and heating the reaction contents. Alternatively, magnetic stirrers may be placed in the vessels and the reactor block may be placed on a heater/stirrer plate to afford agitation and heating. Known liquid-handling robots may be used to dispense reactants, etc. into the batch parallel reactors, but manual dispensing may also be used.

Screens may be performed after the reaction of interest has taken place. Such screens are typically for a property or a chemical of interest. In addition to the screens discussed above, screens include solid-phase staining, as disclosed in U.S. patent application Ser. No. 09/067,448, filed Apr. 27, 1998, which is incorporated herein by reference. Solid-phase staining uses stains to determine if a desired chemical transformation has taken place by either observing a color change or the lack of a color change in a dye that is inserted into the reaction of interest. Parallel TLC may also be used as a screen in this invention, as disclosed in U.S. patent application Ser. No. 09/062,128, filed Apr. 17, 1998, which is incorporated herein by reference. A depolarized light scattering array may screen the reactions of interest in an apparatus and method disclosed in U.S. patent application Ser. No. 09/174,986, filed Oct. 19, 1998, which is incorporated herein by reference. Also, rapid thermal analysis, using a sensor array may be used, as disclosed in U.S. patent application Ser. No. 09/210,485, filed Dec. 11, 1998, which is incorporated herein by reference. Those of skill in the art will recognize that NMR, GC/mass spectrometry, and LC/mass spectrometry, which are commercially available, may also be used for screening product libraries. Finally, rapid polymer characterization techniques may be used, as discussed in U.S. Provisional Patent Application No. 60/080,652, which is incorporated herein by reference.

One method and system disclosed herein utilizes a parent ligand library having a plurality of member ligands as an initial starting point in generating one or more catalyst libraries. In some embodiments, an important feature of the parent ligand library is chemical diversity within the library. This invention will allow such chemically diverse ligand species to be tested parallel. In other embodiments, a single or few ligands will be used repeatedly in a variety of reactions under a variety of conditions for optimization of a reaction with a particular catalyst. With the parent ligand library provided, the next step is optional and entails forming one or more daughter libraries 200 from the parent library 10, as shown in FIG. 2. Literally, a liquid pipette, operated either manually or automatically (e.g., robotically), draws a bit of liquid member ligand 100 from the ligand library 10 at point 70 and dispenses that aliquot into another container to give a daughter library member ligand 202. Point 70 in FIG. 2 can be considered a daughtering station. In accord with this invention, a portion of the ligand library 10 may be daughtered at least once to create one daughter library 200. Thus, creation of the one or more daughter libraries 200 may be only for a portion of the ligand library 10 member ligands 100. More typically, however, each member of the ligand library is daughtered to one or more daughter libraries 200, as is shown in FIG. 2. After the daughtering step, the daughter libraries 200 may be dried or stored in a manner similar to the parent ligand libraries. In other embodiments, the member ligands 100 of the ligand library 10 are maintained in a solid form. During the daughtering process known solid handling equipment and methods are used to take the aliquot from the ligand library to created the daughter library, which will have members that are also solids. Thereafter, it may be necessary to dissolve the member ligands 202 of the daughter libraries 200 in a solvent. The daughtering process is optional because one may go directly from ligand synthesis to catalyst formation; however, this has the disadvantage of using the entire ligand library, meaning that the member ligands in the ligand library must be re-synthesized for experimentation beyond the first reaction or screening experiment.

Once the daughter libraries are formed (or using the ligand library), and continuing with FIG. 2, one or more metal precursors 204 are added to at least a portion of the members 202 of the daughter libraries 200 to create one or more libraries of target metal-ligand complexes, e.g., catalyst libraries 220. Combining may take place at one or more daughtering stations or one or more combining stations. Each of the components or members or libraries to be combined is provided at the daughtering or combining station and known robotic techniques may be used to transfer such components to the daughtering or combining station. Another option shown in FIG. 2 is to create daughter catalyst libraries 222 from the catalyst library 220 by taking one or more aliquot from the catalyst library. This may be done at a daughtering station after at least the metal precursors and ligands have been combined, with or without ligand modifiers or activators. This catalyst daughtering option may also be used when different activating options are being researched for the same ligand metal precursor combinations. Additionally, this option may be desirable when the same catalyst library will be tested for different reactions of interest or when the same catalyst library will undergo the same reaction of interest at different reaction conditions, such as with an optimization research and development program.

Once the catalyst libraries 220 or daughter catalyst libraries 222 are prepared, the members 221, 223 are subjected to a reaction of interest at either a reactor station or a screening station. Reactions of interest may be performed in parallel or in a serial fashion. Different reactions of interest may be performed on daughter catalyst libraries or catalyst libraries. Referring again to FIG. 2, the catalyst library 220 may follow path X and be daughtered as discussed above into daughter catalyst libraries 222. Path X shows a research path including either (1) reaction with screening or (2) reaction and subsequent screening. Each catalyst library 220, 222 is tested in a reaction of interest at a reaction station 80 to create one or more product libraries 224. In parallel or serial fashion, the reactants are added to the reactor with the catalyst members and the reaction is performed under predetermined conditions. If a reactor is chosen with sensing capabilities, then screening may take place during the reaction. After the reaction, the results may be tested in post reaction screening 90 for a property or a compound or a material. For example, if a small molecule transformation, such as aryl amination, is the reaction of interest then staining may be used to determine if the transformation has occurred by choosing a stain appropriate for the product or reactant.

Path Y in FIG. 2 shows a research path having multiple reactions and screens. The catalyst library 220 is daughtered into daughter catalyst libraries 222 with the daughter libraries each being screened in a primary screen 110. A primary screen is one that runs the reaction of interest, and provides sufficient data to determine at least whether a catalyst member was active in the reaction of interest or whether a product of interest was formed in the reaction. A primary screen may be one where the catalysts or products are not separated from each other, but subjected together to the reaction of interest in a parallel optical screen. For example, if the reaction of interest is the polymerization of ethylene, the primary screen may be a chamber that allows ethylene to contact all catalyst library members simultaneously. The active catalysts may be identified from the inactive or less active catalyst by encoding the catalyst members of the catalyst library, as disclosed in copending U.S. patent application Ser. No. 09/033,207, filed Mar. 2, 1998, which is incorporated herein by reference. The primary screen may be an infrared screen that identifies active catalysts by heat of reaction, such as disclosed in copending U.S. patent application Ser. No. 08/946,135, filed Oct. 7, 1997, which is incorporated herein by reference (published as WO 98/15815, which is also incorporated herein by reference). The primary screen may be another optical technique to determine if a product has been made; for example, if the reaction of interest is an emulsion polymerization, the optical screen may determine if an emulsion was created. Useful optical techniques are disclosed in copending U.S. patent application Ser. No. 08/947,085, and filed Oct. 8, 1997, which is incorporated herein by reference (published as WO 98/15805, which is also incorporated herein by reference). Another possible primary screen is a parallel thin layer chromatography system, as disclosed in U.S. Pat. No. 09/062,128, filed Apr. 17, 1998 and incorporated herein by reference. Other primary screens may be known or developed by those of skill in the art for specific reactions of interest.

Any screen may be a primary screen, however, the object of having a primary screen is to eliminate some of the members 221, 223 of the catalyst libraries or daughter catalyst libraries from further, more detailed testing. Since an enormous number of ligands and metal precursors are typically being combined in different routes, it may be that one route is not applicable for a particular metal precursor/ligand combination. A primary screen would eliminate such an inapplicable route at a lower cost than a screen that provides more detailed information. As such primary screens are designed to quickly, effectively and/or efficiently reduce the number of catalyst members that are screened for detailed information (such as conversion and selectivity or polymer particle size).

Path Y also shows that after the primary screen 110, members of catalyst or product 10 libraries 220, 222, 224 that pass the primary screen are sent to a secondary screen 112. The secondary screen runs the same reaction of interest under conditions that supply more data than the primary screen. Any of the screens discussed above may be a primary or secondary screen. Another feature of FIG. 2 is a feedback loop 95 that provides information for the synthesis of new parent libraries or new daughtering. The information comes from a post reaction screen 90, a reaction that includes a screen 80, a primary screen 110 or a secondary screen 112. For example, the information sent in the feedback loop 95 may be catalyst activity, compound existence or disappearance, polymer properties or any other information that comes from the screens that are performed. This feedback loop may be such as disclosed in U.S. Pat. No. 5,563,564, herein incorporated by reference.

It will be readily apparent to those of skill in the art that the foregoing reaction and/or screening methods are intended to illustrate, and not restrict the ways in which the catalyst or product libraries can be screened for useful properties for a reaction of interest. Other screening techniques and apparatuses known to those having skill in the art may similarly be employed.

Figure 5:
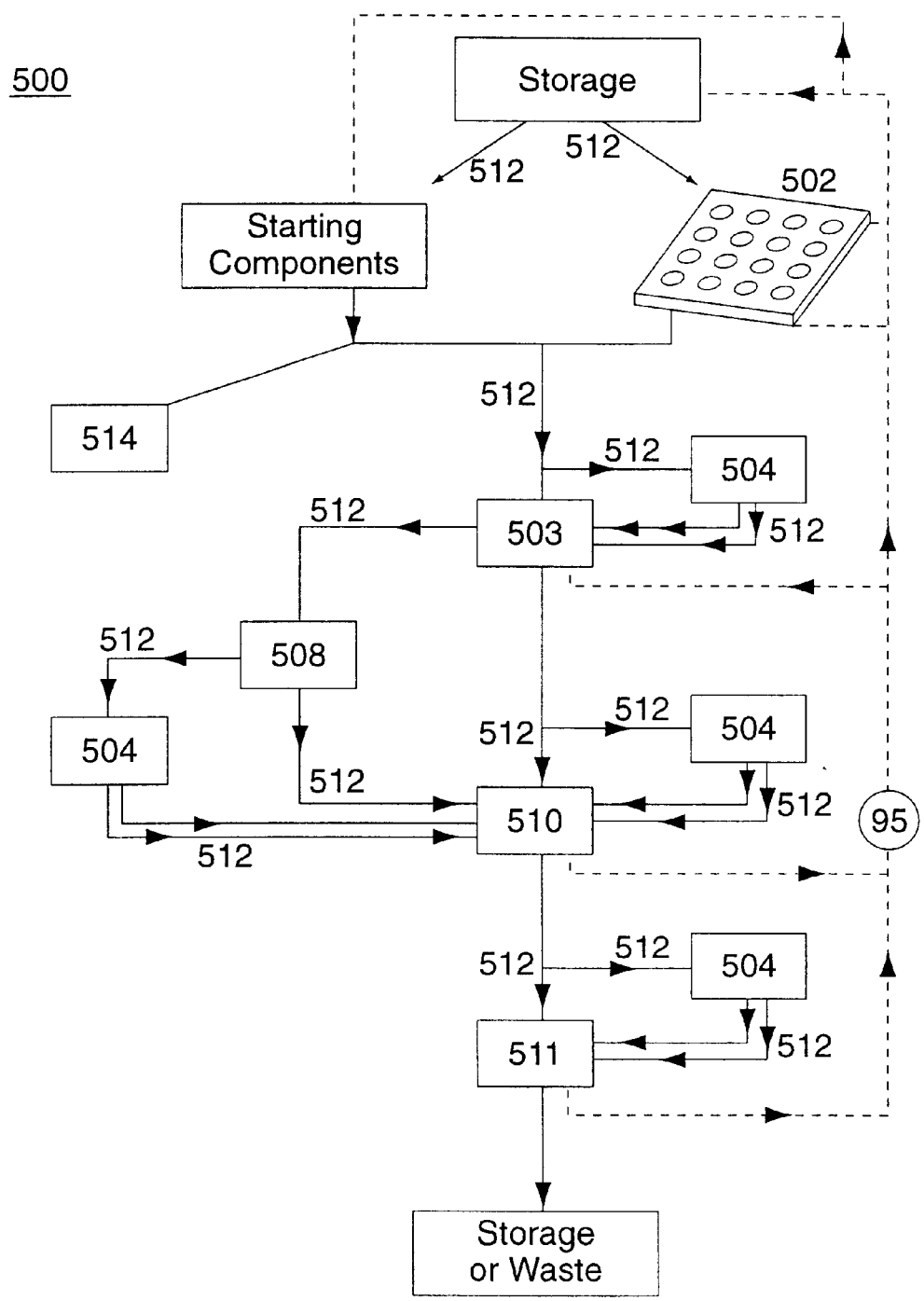
FIG. 5 is block diagram illustration of an overall method and apparatus of this invention.

An apparatus or system 500 for researching for novel ligands, catalysts or products is illustrated in FIG. 5. System 500 includes a parent library 502, a combining station 503, a daughtering station 504 (to create one or more daughter libraries 506), optionally a filtering station 508, a reaction station 510, a screening station 511 and an automated robotic system, represented by arrows 512 to move libraries from one station to another. As used herein a "station" is a location in the apparatus that performs one or more functions. The functions may be combining the starting components, combining ligands with metal atoms, ions or precursors, creating a product library via a reaction, screening or any of the other functions discussed above. Thus, the station may comprise a liquid handling robot with pumps and computers (as known in the art) to dispense, dissolve, mix and/or move liquids from one container to another. The station may include any of the reactors discussed above, and may be in an inert atmosphere glove box. A location in the apparatus may perform multiple functions, but for purposes of discussing the methodology in block diagram form, each location or station herein will be referred to as a separate station.

Basically, starting components or parent ligand libraries or metal precursors, etc. are inputted into the apparatus (or retrieved from storage) and sent to a combining station 503. After combination, the product library is formed via reaction at the reaction station 510. If screening does not occur during the reaction, the product library is sent to the screening station 511 for screening as discussed above. A daughtering station 504 can be inserted into the process to create daughter libraries 506. As discussed above, when ligands are being combined with metal precursors, this takes place at the combining station. Finally, a filtering station 508 may be used when solid phase agents are used in the process.

FIG. 5 illustrates a block diagram flow for a methodology useful in this invention. Starting components or parent libraries may be maintained in storage and retrieved from storage and moved via the handling system 512 to the combining station 503. Optional in this process is the daughtering of the parent library at the daughtering station 504. Multiple paths are shown from the daughtering station 504 to the combining station 503 to show the possibility that multiple daughter libraries are transferred to the combining station 503. The combining station combines the starting components together in a predefined manner, using the components, ratios, etc. as discussed above. Typically, exiting the combining station 503 is either a catalyst library or a combination of components for turning into a product library. One option is for the results of the combination to go to a filtering station 508. Since filtering removes unwanted materials from the library (typically from the catalyst library), it may be desirable to daughter the library after filtering, which is accomplished at a daughtering station 504 between the filtering station 508 and the reaction station 510. The catalyst library or combination of starting components proceeds to a reaction station 510, where the product library is formed. In other words, the reaction of interest is run at the reaction station 510. Process diversity is accomplished at the reaction station 510 using the reaction options discussed above. From the reaction station 510, the product library proceeds to the screening station 511, where a predetermined screen is run to determine if the reaction of interest was successful and/or the qualitative or quantitative degree of success of the reaction of interest. The screening station may include a single screen or multiple screens (such as a primary and secondary screen) and may entail using multiple locations for the multiple screens. A feed-back loop 95 is provided that takes screening information from either the reaction station 510 (when a reaction that includes a screen is used) or the screening station 511. This screening information is used at the combining station 503 for new combinations of starting components or creating new catalyst libraries, etc. The feed-back loop 95 may also feed screening information to the starting components or parent libraries or the storage location for new product libraries to be created for making a product of interest.

The system 500 includes a computer or processor based system 514 that controls, monitors and/or coordinates the process steps as well as interaction between the various stations 503, 504, 508, 510 and 511. The "control" system also coordinates the movement of plates (parent or daughter) moving in the robotic system 512. The "control" system 514 also includes computers, processors and/or software that a user (e.g., chemist) may use to interact with the system 500. Ideally, the control system 514 contains sufficient hardware and software so that it is "user-friendly", for example so that the amount of input by the user is limited to the essential design and process elements. The control system 514 can comprise a central computer or processor to command, control and monitor each subsystem or station or piece of the system 500. Alternatively, the control system 514 can comprise an integrated architecture with one or more of the subsystems, stations or pieces is a smart system of its own right. Thus, a user of the "control" system 514 may design a set of experiments to create a product library, specify the screen of that product library and command the system to perform all the chemistry and screening automatically from chemicals in storage.

For example, the "control" system 514 may command transportation of a library plate from storage to a combining station giving instructions to the combining station that specify the types and volumes of chemicals to dispense. Another similar example is where similar instructions are used with a daughtering station. The "control" system 514 may also control the robotics 512 to move chemicals to the various stations 503, 504, 508, 510 and 511. As a further example, the "control" system 514 may monitor and control the time that a plate remains at a station or the time that a reaction of interest is allowed to run, such as by instructing a robot to add a catalyst kill to reactor vessels at various times. Still further, the "control" system may monitor and control a screen, such as by moving a product library to the screening station and instructing an auto-sampling robot to sample the product library with particular solvents for injection and into a molecular weight screen. Additionally, the "control" system 514 may collect, manipulate and/or store screening data. For example, the "control" system 514 may take data from a screen, reduce that data and then send the data for storage to a database. The "control" system 514 can also monitor the system 500 for safety, problems or other process issues. The "control" system may also include the feed-back loop 95, discussed elsewhere.

For example, robotic system 512 preferably includes an automated conveyer, robotic arm or other suitable device that is connected to the "control" system 514 that is programmed to deliver the library plate 502 or daughter plates 506 to respective stations 503, 504, 508, 510, 511. The processor is programmed with the operating parameter using a software interface. Typical operating parameters include the coordinates of each of stations 503, 504, 508, 510, 511 in the system 500 as well as both the library storage plate and daughter plates positioning locations at each station. Other data, such as the initial compositions of each ligand modifier, metal precursor, activator and the initial compositions of the ligands may also be programmed into the system.

Figure 6A:
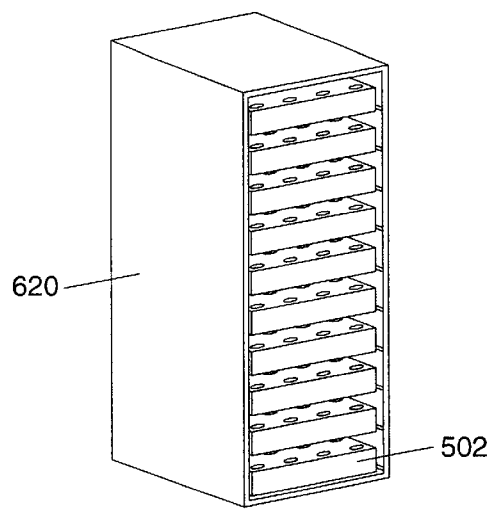
FIG. 6 includes FIGS. 6A–6C and shows details of a library storage rack and plate system useful in this invention.
Figure 6B:
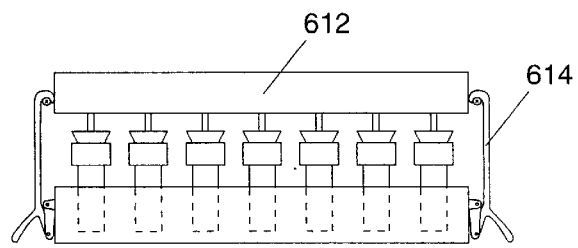
Figure 6C:
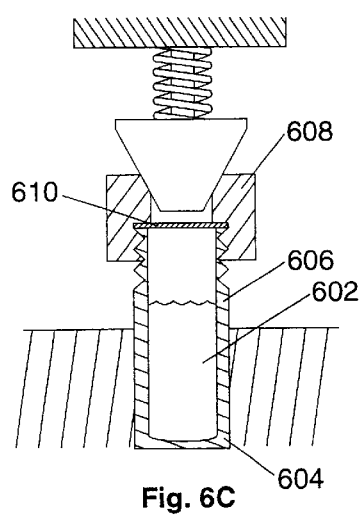

In some embodiments, a library is stored in a storage plate 502, as more clearly seen in FIG. 6B. The library storage plate 502 includes a number of wells 604 formed therein that receive vials 606 containing the library members, as shown in FIG. 6C. Each vial 606 may be provided with a cap 608 having a septum 610 for protecting the members when being stored. An optional lid 612 having latches 614 shown in FIG. 6B for connecting to the storage plate 502 may also be provided for storage purposes. FIG. 6A also shows that the library plate 502 may be stored in a rack 620 prior to transfer to the next station, such as a combining station 503 or daughtering station 504.

Figure 7:
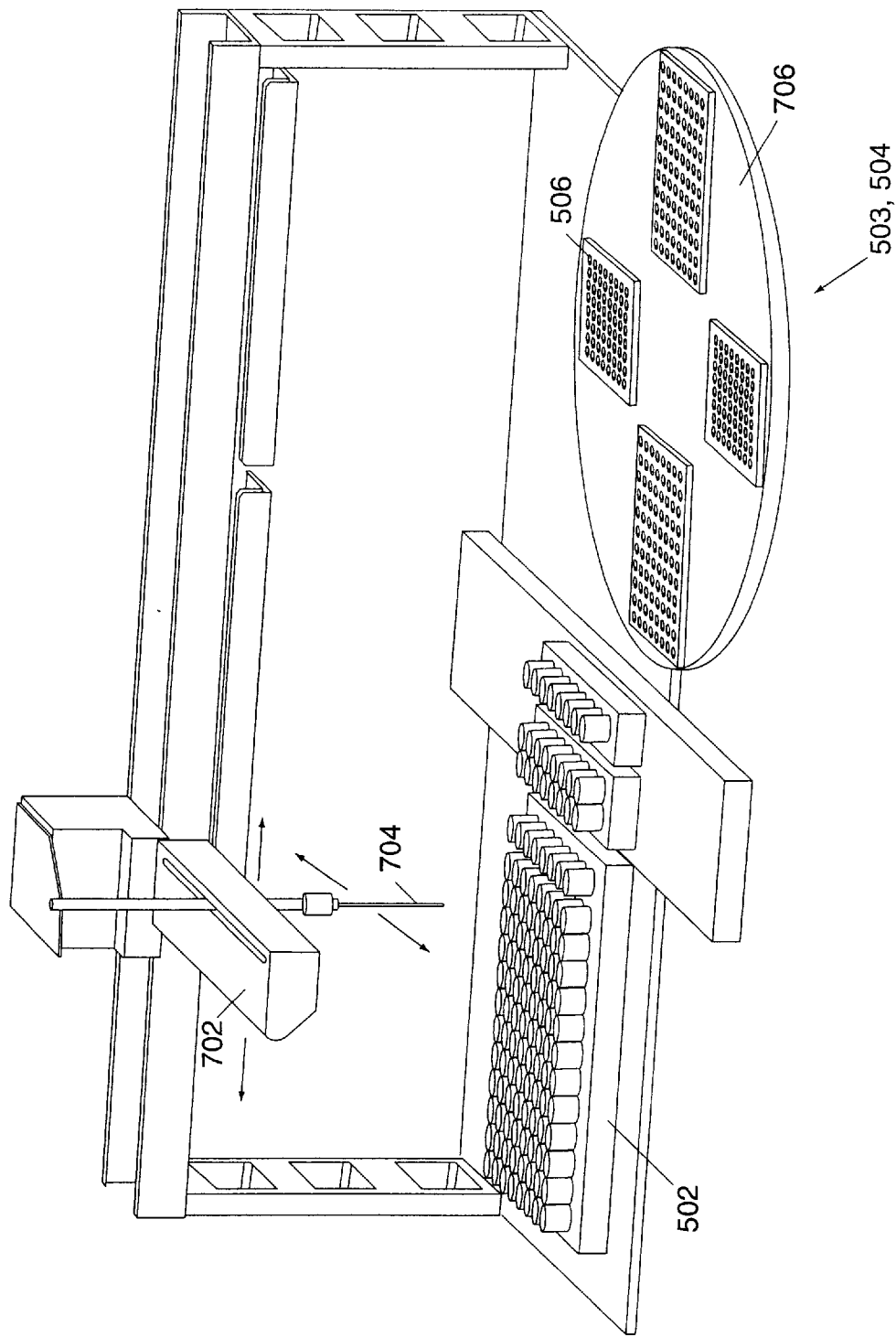
FIG. 7 is a partial view of one embodiment of the apparatus of this invention.

In a preferred embodiment, referring to FIG. 7, a combining station 503 or a daughtering station 504 includes a daughtering robotic arm 702 that carries a movable probe 704 and a turntable 706 for holding multiple daughter plates 506 while the daughtering step is being performed. Daughtering robotic arm 702 is movable. The robotic system 512 manipulates the probe 704 using a 3-axis translation system. The probe 704 is movable between vials of ligand modifiers, metal precursors, and activators arranged adjacent the synthesis station and plate.

Once the product libraries are created, the robotic handling system 512 next transports plates to a screening station 511. As this system may be configured to perform multiple screening steps using multiple screening techniques, and there may be more than one screening station. It is preferred that plates containing the libraries each are each receivable in a reactor blocks for the screening operation. Indeed, the plates may be the reactor block that is moved from one station to the next. As-disclosed in the copending applications, in one embodiment, the reaction block generally contains heating elements and temperature sensing devices—thermocouples, thermistors, RTD's and other similar devices—that communication with a processor. The heating elements, temperature sensing devices, and the processor comprise a temperature control system that maintains the temperature of each of the catalyst library members at a pre-selected temperature during the reaction such that the catalysts may be analyzed as a function of temperature.

EXAMPLE

This an example of rapid light scattering screening of a combinatorial library that was prepared by controlled radical polymerization.

In a dry, nitrogen atmosphere glovebox stock solutions were prepared using ligand L-1 having the structure shown below:

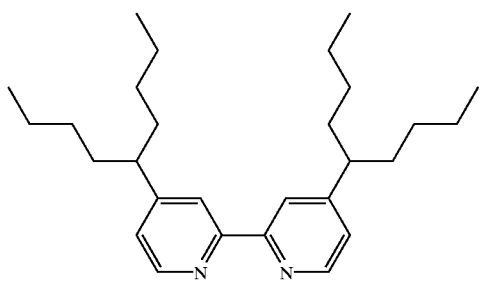

L-1

L-1 was synthesized from reductive coupling of 4-(5-nonyl)pyridine using Pd/C catalyst at 200° C.

1-chloro-1-phenylethane (hereinafter "I-1") was synthesized by treatment of styrene with HCl and purified by distillation. I-2 was synthesized by reaction of commercially available divinylbenzene with HCl, followed by purification by distillation. I-2 had the following structure:

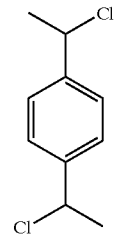

All other materials were commercially available and were purified using conventional techniques.

Five stock solutions were prepared in a dry nitrogen atmosphere glovebox (I, II, III, IV, and V), as follows: Solution I comprised 19.8 mg (0.141 mmol) of 1-chloro-1-phenylethane (I-1) and 800 μL (6.98 mmol) of styrene. Solution II comprised 20 mg (0.2 mmol) CuCl, 174 mg of L-1 (0.42 mmol), and 3.33 mL (29.1 mmol) of styrene. Solution III comprised 14.2 mg of I-2 (0.07 mmol) and 800 μL (6.98 mmol) styrene. Solution IV comprised 14.7 mg (0.105 mmol) of I-1, 10.4 mg (0.105 mmol) CuCl, 90 mg (0.022 mmol) of L-1, and 6 mL (52.4 mmol) of styrene. Solution V comprised 10.7 mg (0.0525 mmol) of I-2, 10.4 mg (0.105 mmol) CuCl, 90 mg (0.022 mmol) of L-1, and 6 mL (52.4 mmol) of styrene.

A 7-row by 12-column 84-vessel glass-lined aluminum reactor block array with approximately 800 μL volume per vessel was prepared in a drybox under dry nitrogen atmosphere and stock solutions I–V were manually distributed to the vessels using a metering pipettor, such that elements 1–5 received a gradient of Solution I (100 μL, 50 μL, 33.3 μL, 25 μL, and 20 μL), 100 μL of Solution II, and a gradient of excess styrene (0 μL, 50 μL, 66.7 μL, 75 μL, 80 μL). Elements 6–10 received a gradient of Solution III (100 μL, 50 μL, 33.3 μL, 25 μL, and 20 μL), 100 μL of Solution II, and a gradient of excess styrene (0 μL, 50 μL, 66.7 μL, 75 μL, 80 μL). Elements 11–15 received a gradient of Solution I (100 μL, 50 μL, 33.3 μL, 25 μL, and 20 μL), 100 μL of Solution II, a gradient of excess styrene (0 μL, 50 μL, 66.7 μL, 75 μL, 80 μL), and 200 μL of diphenylether. Elements 16–20 received a gradient of Solution III (100 μL, 50 μL, 33.3 μL, 25 μL, and 20 μL), 100 μL of Solution II, a gradient of excess styrene (0 μL, 50 μL, 66.7 μL, 75 μL, 80 μL), and 200 μL of diphenylether. Elements 21–50 (a 5×6 array) received 150 μL of Solution IV and a gradient of dilutions along each row by adding solvent (75 μL, 150 μL, 225 μL, 300 μL, 375 μL, 450 μL) with a different solvent in each row (diethyl carbonate, benzene, o-dichlorobenzene, m-dimethoxybenzene, and diphenylether, respectively). Similarly, elements 51–80 (a 5×6 array) received 150 μL of Solution V and a gradient of dilutions along each row by adding solvent (75 μL, 150 μL, 225 μL, 3 00 μL, 3 75 μL, 450 μL) with a different solvent in each row (diethyl carbonate, benzene, o-dichlorobenzene, m-dimethoxybenzene, and diphenylether, respectively). In this fashion an array of 7×12 diverse polymerization reactions were prepared, requiring a setup time of approximately 5 hrs. The reactor block array was sealed using a Teflon membrane covering a silicon rubber sheet compressed with an aluminum plate bolted in place.

The reactor block array was then heated to 120° C. for 15 hrs with agitation provided by an orbital shaker. The reactor block array was allowed to cool, and to each vessel was added THF such that the total volume reached 0.8 mL, and the block was re-sealed and heated at 105° C. with orbital shaking for approximately 1 hr, to allow formation of homogeneous fluid solutions. The reactor block was then allowed to cool.

Figure 4:
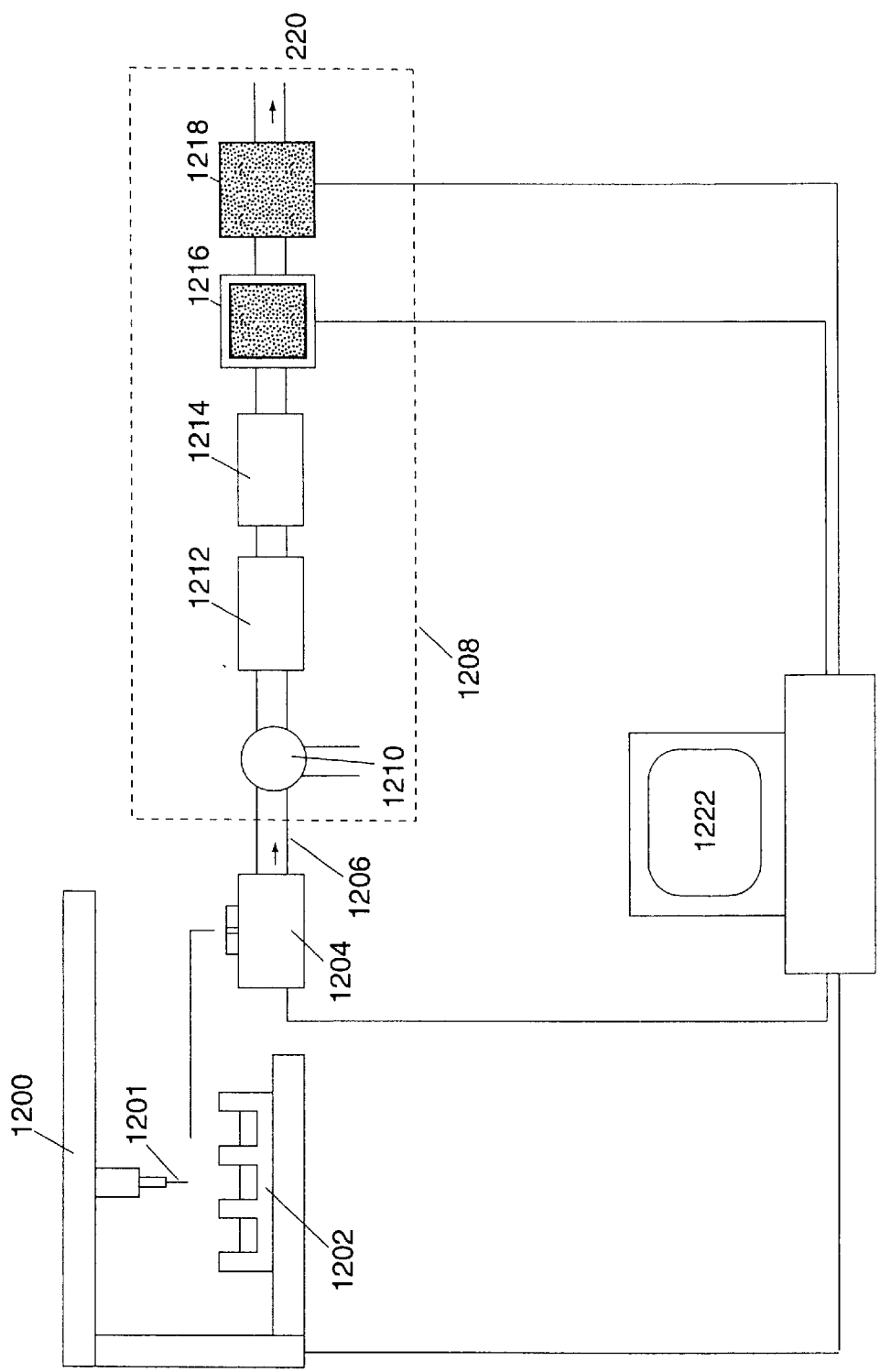
FIG. 4 is a block diagram illustration of rapid molecular weight light scattering characterization equipment that was used in the Example.

Each element of the array was analyzed by rapid manner using the following equipment and method:

FIG. 4 shows the general layout of the equipment including an eight port valve 1210 and a filter 1212. A light scattering detector 1216 and a RI detector 1218 were used. Samples were injected into the 8-port valve, having two 50-μl injection loops and the system was maintained at a temperature of 36° C. A short chromatographic column 1214 (Polymer Laboratories, 1110–1520, sold as a GPC guard column) was in-line between the filter 1212 and the light-scattering cell 1216. Samples were manipulated with a sampler 1200 automatically. The sampler 1200 had a tip 1201 that obtained the polymer sample from the sample tray 1202. The sampler 1200 moved the tip 1201 into a loading port 1204 that sent the sample through the transfer line 1206. The system was controlled by a single computer 1222 that controlled the sampler 1200, loading of the sample via the loading port 1204, as well as collecting data from the light scattering detector 1216 and the RI detector 1218.

$M_w$ for each sample was calculated using an algorithm incorporated in the analysis software ("Precision Analyze", version 0.99.031(06/08/97), Precision Detectors) accompanying the PD2020. In order to determine $M_w$, points in the chromatogram representing the baselines of the 15 and 90 degree signals and the RI signals were first selected ("baseline regions"). Linear least-squares fits of these points defined the three baselines. Then, an integration region encompassing the main sample peak was chosen. The software then calculates $M_w$, based on the SLS and RI data and baseline values in this integration region. The calculation was performed in the limit of the radius of gyration, $R_g$, being much less than the measurement wavelength, and the polymer concentration in the dilute limit representing isolated molecules. This calculation also used the angular form-factor, $P(\theta)$, appropriate for a Gaussian-coil molecule, and fitted it to the SLS signals to extract $M_w$. For polymers with $M_w$ less than about 10,000 kD, this method determined values of $M_w$ within less than 5% of values calculated assuming non-Gaussian-coil forms of $P(\theta)$.

$R_h$ is calculated from the diffusion constant of the polymer molecules, which is obtained by fitting the photon-photon correlation function to an exponential. The PD2020 system was designed to allow for measurements of $R_h$ at each time-slice of the chromatogram for sufficiently low flow rates.

Using a programmable robotic sampler, 20 μL of each reactor were drawn and dispensed along with 250 μL of THF into a polypropylene microtiter plate. 100 μL of this diluted sample was drawn and used to load a 50 μL sample loop on an HPLC injector, followed by rapid light scattering evaluation. During the time of each analysis, the step of diluting the next sample was conducted, so that each sample injection automatically occurred at 40 sec. intervals. Table 1, below, shows the average $M_w/1000$ of the samples derived from the analysis.

TABLE 1

| Col> | 1 | 2 | 3 | 4 | 5 | 6 | 7 | 8 | 9 | 10 | 11 | 12 |
|---|---|---|---|---|---|---|---|---|---|---|---|---|
| Row 1 | 22.2 | 35.7 | 46.3 | 55.8 | 63.7 | NR | NR | 25.9 | 47.6 | 57.3 | 72 | 78.2 |
| 2 | 8.65 | 15 | 22.3 | 26.6 | 30.4 | NR | NR | 11.2 | 19.8 | 33.1 | 40.1 | 42.9 |
| 3 | 28.9 | 20.2 | 16.6 | 12.6 | 12 | 11.9 | 44 | 34.3 | 29.8 | 20.9 | 17.6 | 16.4 |
| 4 | 38.9 | 29.6 | 26.1 | 24.1 | 24.2 | 22.9 | 56 | 51.7 | 45 | 38.7 | 30.9 | 27 |
| 5 | 47.8 | 34.8 | 23.6 | 18.6 | 15.4 | 14.1 | 59.9 | 48.3 | 33.7 | 25.2 | 22.6 | 18.3 |
| 6 | 40.6 | 28.6 | 15.3 | 12.9 | 12 | 13.1 | 45.8 | 20.8 | 17.7 | 12.3 | 13.3 | 13.8 |
| 7 | 40.3 | 30.2 | 23.2 | 20.9 | 19.5 | 19.2 | 46.8 | 37.4 | 34.2 | 29.7 | 28.6 | 27.8 |

The expected trends of decreasing molecular weight with increasing dilution, and decreasing molecular weight with decreasing monomer to initiator ratio were observed. This demonstrates very rapid molecular weight determinations in combinatorial discovery of optimal catalytic processes.

It is to be understood that the above description is intended to illustrative and not restricted. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A system for researching for novel catalyst libraries, comprising:

a ligand library storage plate containing a plurality of ligand library member ligands, wherein said member ligands have a common scaffold but vary in structural diversity;

a daughtering station wherein a plurality of daughter libraries are formed by taking one or more aliquots from one or more member ligands of said ligand library;

a plurality of daughter plates for storing said daughter libraries;

a combining station wherein metal precursors are added to at least a portion of said daughter libraries to create a plurality of catalyst libraries; and a reaction station wherein at least a portion of said catalyst libraries are subjected to a reaction of interest.

2. The system of claim 1 further comprising a filtering station between said combining station and reaction station.

3. The system of claim 1 further comprising a screening station that receives the libraries from said reaction station and screens the contents thereof for a compound or property of interest.

4. The system of claim 3 wherein a control system collects data from said screening station and stores such data in a database.

5. The system of claim 3 wherein said screening station is equipped to screen the contents of the libraries for molecular weight.

6. The system of claim 3 wherein said screening station is equipped to screen the contents of the libraries for particle size.

7. The system of claim 3 wherein said screening station is equipped to screen the contents of the libraries using Infrared thermography, Fourier Transform Infrared spectroscopy, thin layer chromatography, mass spectroscopy, gas chromatography or nuclear magnetic resonance.

8. The system of claim 1, further comprising an automated robotic system for forming said catalyst libraries and transferring said storage plates and daughter plates between said stations in said system.

* * * * *